United States Patent [19]
Fields

[11] Patent Number: 5,088,984
[45] Date of Patent: Feb. 18, 1992

[54] MEDICAL CONNECTOR

[75] Inventor: Charlie B. Fields, Ypsilanti, Mich.

[73] Assignee: Tri-State Hospital Supply Corporation, Howell, Mich.

[21] Appl. No.: 592,134

[22] Filed: Oct. 3, 1990

[51] Int. Cl.⁵ .......................................... A61M 5/178
[52] U.S. Cl. ................................. 604/167; 604/284; 604/905
[58] Field of Search ............... 604/164, 165, 166, 167, 604/168, 256, 280, 283, 284, 247, 905, 169

[56] References Cited

U.S. PATENT DOCUMENTS

| | | |
|---|---|---|
| D. 287,882 | 1/1987 | Glash . |
| D. 288,005 | 1/1987 | Glash . |
| 3,097,646 | 12/1960 | Scislowicz . |
| 3,484,121 | 9/1966 | Quinton . |
| 3,502,097 | 6/1966 | Muller . |
| 3,752,510 | 8/1973 | Windischman et al. . |
| 3,851,647 | 12/1974 | Monestere, Jr. et al. . |
| 3,865,938 | 4/1975 | Mellor . |
| 3,986,508 | 10/1976 | Barrington . |
| 4,019,512 | 4/1977 | Tenczar . |
| 4,161,946 | 7/1979 | Thanawalla . |
| 4,187,846 | 2/1980 | Lolachi et al. . |
| 4,244,379 | 1/1981 | Smith . |
| 4,317,445 | 3/1982 | Robinson . |
| 4,323,065 | 4/1982 | Kling . |
| 4,338,933 | 7/1982 | Bayard et al. . |
| 4,354,492 | 10/1982 | McPhee . |
| 4,362,156 | 12/1982 | Feller, Jr. et al. . |
| 4,370,987 | 2/1983 | Bazell et al. . |
| 4,373,535 | 2/1983 | Martell . |
| 4,378,812 | 4/1983 | Sarstedt . |
| 4,379,506 | 4/1983 | Davidson . |
| 4,380,234 | 4/1983 | Kamen . |
| 4,391,029 | 7/1983 | Czuba et al. . |
| 4,398,544 | 8/1983 | Nugent et al. . |
| 4,412,573 | 11/1983 | Zdeb . |
| 4,416,291 | 11/1983 | Kaufman . |
| 4,417,886 | 11/1983 | Frankenhouser et al. . |
| 4,418,703 | 12/1983 | Hoch et al. . |
| 4,421,123 | 12/1983 | Percarpio . |
| 4,426,024 | 1/1984 | Hogan et al. . |
| 4,439,188 | 3/1984 | Donnebet et al. . |
| 4,457,749 | 7/1984 | Bellotti et al. . |
| 4,468,224 | 8/1984 | Enzmann et al. . |
| 4,511,359 | 4/1985 | Vaillancourt . |
| 4,535,820 | 8/1985 | Raines . |
| 4,547,194 | 10/1985 | Moorehead . |
| 4,603,152 | 7/1986 | Laurin et al. . |
| 4,653,513 | 3/1987 | Dombrowski . |
| 4,655,750 | 4/1987 | Vaillancourt . |
| 4,660,570 | 4/1987 | Dombrowski . |
| 4,673,396 | 6/1987 | Urbaniak . |
| 4,673,400 | 6/1987 | Martin . |
| 4,698,061 | 10/1987 | Makaryk et al. . |
| 4,711,637 | 12/1987 | Leigh et al. . |
| 4,713,057 | 12/1987 | Huttmer et al. . |
| 4,743,243 | 5/1988 | Vaillancourt . |
| 4,752,292 | 6/1988 | Logan et al. . |
| 4,850,961 | 7/1989 | Wanderer et al. . |
| 4,857,062 | 8/1989 | Russell ................. 604/256 |
| 4,929,235 | 5/1990 | Merry et al. .......... 604/167 |
| 4,935,010 | 6/1990 | Cox et al. ............. 604/167 |

*Primary Examiner*—John D. Yasko
*Attorney, Agent, or Firm*—Brooks & Kushman

[57] ABSTRACT

A medical connector (10) disclosed comprises first and second connector members (12, 22) including a flashback chamber (26), a needle (20) penetrable into said chamber and an improved one-way valve (32) spaced from said needle for closing said chamber and for establishing fluid communication through the connector (10) when the connector members (12, 22) are joined to administer medication or food to the patient while preventing a patient's blood from entering the chamber (22) and coming in contact with the needle.

7 Claims, 2 Drawing Sheets

MEDICAL CONNECTOR

TECHNICAL FIELD

This invention relates to medical connectors for fluid carrying tubes, and more particularly, to medical connectors for intravenous tubes that communicate fluids to a patient and connectors that minimize risk of contact with the patient's blood.

BACKGROUND ART

Conventional medical connectors used to connect tubing used in intravenous delivery apparatus include a connector having at least two connector members. One of the connector members includes a needle and another of the connector members includes a sealed entry port that is penetratable by the needle to establish fluid communication between the members when the members are connected. The entry port typically comprises resilient material that automatically closes after the withdrawal of the needle.

Typically, the needle is recessed in the cavity of one member so that after termination of the connection, the needle that has been in contact with the patient's blood is not easily contacted by a nurse who is at risk from being stuck by a contaminated needle. Such connectors are disclosed in U.S. Pat. Nos. 4,752,292 and 4,511,359.

These conventional medical connectors however, make no provision preventing a recessed needle from contact with the patient's blood, where the needle could become contaminated.

U.S. Pat. No. 4,511,359 discloses a one-way valve comprised of a biased tubular band fit over a perforated projection permitting pressurized fluid flow in only one direction to keep a fluid connector sterile. The perforated projection therein is impermeable to the introduction of an introducer needle rendering the connector unsuitable for use with a catheter tip. However, the valve structure can be improved upon.

SUMMARY OF THE INVENTION

An object of the present invention is to provide a medical connector for use with the administration of fluids to a patient and having an improved one-way valve prohibiting a needle of the device from contact with the patient's blood.

Another object of the invention is to provide a system wherein modified medical connector members can be used for venipuncture and placement of a catheter in the patient and the subsequent connection can be effected without the needle contacting the patient's blood.

A further object of the invention is to provide a medical connector wherein an introducer needle is shielded from contact by a nurse.

In carrying out the above objects and thus a specific object of the invention, the medical connector for connecting a fluid carrying tube to the patient includes a first connector member having a first recessed open end defining a cavity including internal threads therein. The first connector member also includes a second closed end supporting a needle therein for communicating the fluid from the fluid carrying tube through the closed end to the cavity. The medical connector also includes a second connector member having a distal end partially defining a flashback chamber and adapted to pass through the open end of the first connector member.

The second connector member includes external threads thereon corresponding to the internal threads of the first connector member for joining both connector members. The second connector member includes a rubber septum on the distal end partially defining the flashback chamber and has a yieldable portion adapted to be penetrated by the needle when the first and second members are joined. Joining the first and second members establishes fluid communication through the needle to the flashback chamber without spillage and the rubber septum spontaneously closes when the first and second connectors are separated and the needle is withdrawn from the flashback chamber.

The flashback chamber also has a one-way valve completing the definition of the flashback chamber and spaced from the needle when the first and second connectors are joined. The one-way valve prevents the patient's blood from entering the chamber yet establishes fluid communication through the needle.

Preferably, the second connector member includes a cylindrical open end on the second connector member opposite from the distal end. The one-way valve is a planar washer spanning the open end and is operable in one manner against the open end to close the flashback chamber for preventing blood from entering the chamber and in another manner, away from the open end for passing fluid to the patient. The planar washer is spaced axially from the needle. In this preferred embodiment, the flashback chamber is made from a clear plastic material that allows any blood which accidentally enters the flashback chamber to be viewed.

In another embodiment of the invention, the second connector member of the medical connector includes a branch connection member including first, second and third tubular conduits. The first and second conduits merge into the third and the third is in communication with the cylindrical open end of the second connector member. This construction of the second connector member forms a "Y" connector or piggyback connector.

In yet another embodiment of the invention, the first connector member includes an elongated introducer needle having a tip for venipuncture movably mounted with respect to the second closed end and extendable beyond the first recessed open end and the cylindrical open end of the second connector member when the connector members are joined for introduction of the needle into the patient. The second connector member also includes a catheter tip mounted on the cylindrical open end through which the introducer needle is movable and the catheter tip is in communication with the flashback chamber. The catheter tip is inserted by the introducer needle into the patient and the one-way valve in this embodiment comprises a resilient material which closes off a hole in the valve produced by the introducer needle as the needle is moved into and out of the valve during the application of the catheter into the patient.

Preferably, the first connector member includes a needle guard extending from the second closed end. The needle guard includes an elongated guide, including a stop, housing the introducer needle. The elongated introducer needle also includes a latch mechanism on the end opposite from the tip and cooperable with the stop to hold the introducer needle in a retracted position where the tip of the introducer needle is recessed within the first recessed open end of the medical connector.

The above objects and other objects, features, and advantages of the present invention are readily apparent from the following detailed description of the best mode for carrying out the invention when taken in connection with the accompanying drawings.

BEST MODE FOR CARRYING OUT THE INVENTION

Figure 1:
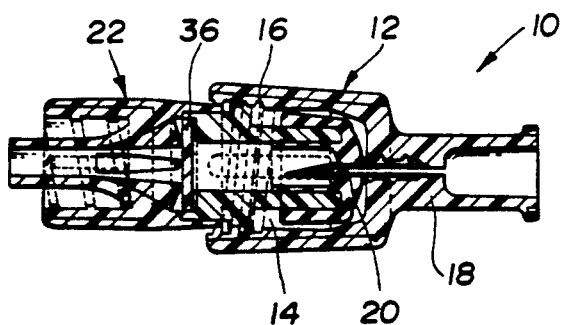
FIG. 1 is a sectional elevational view of a medical connector constructed in accordance with a first embodiment of the present invention.

Referring to FIG. 1 of the drawings, a medical connector constructed in accordance with the present invention is generally indicated by reference numeral 10 and is used for connecting a fluid carrying tube T to a patient. As is hereinafter more fully described, the apparatus 10 provides an economical connector that prohibits contact between a nurse and the patient's blood. The medical connector 10 is also easily modified into alternative embodiments and these embodiments form an economical and convenient system for establishing an intravenous connection with the patient and subsequently administering medication intravenously to the patient.

Figure 2:
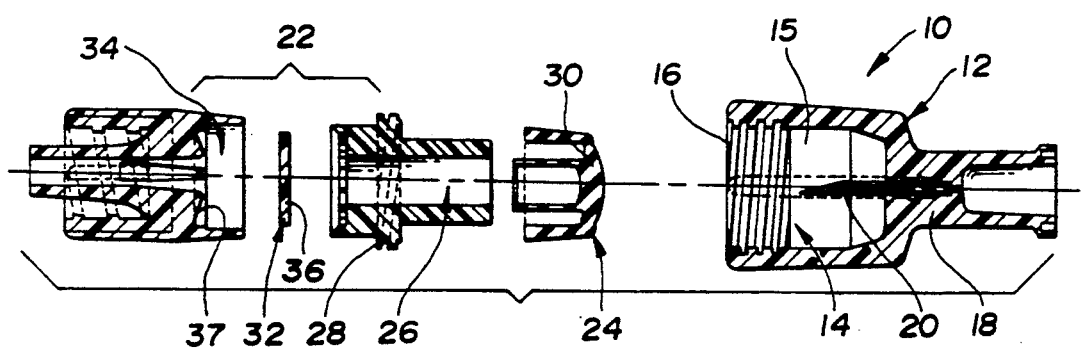
FIG. 2 is an exploded sectional elevational view of the medical connector of FIG. 1.
Figure 7:
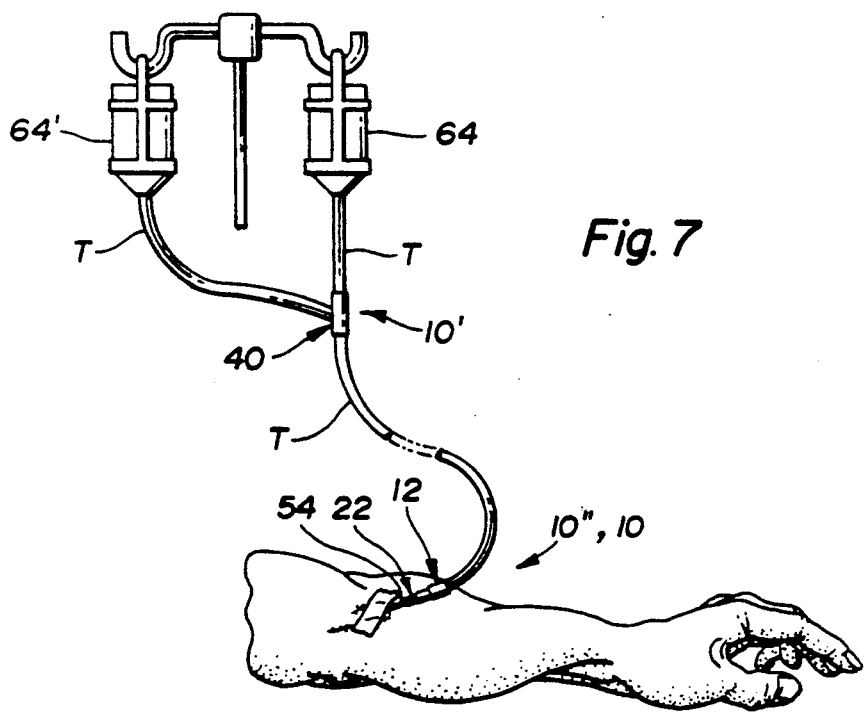
FIG. 7 is a schematic view illustrating administering a medication intravenously to the patient in accordance with convention practice.

Referring to FIGS. 1 and 2 of the drawings, medical connector 10 includes a first connector member 12 having a first recessed open end 14 defining a cavity 15 including internal threads 16 therein. First connector member 12 includes a second closed end 18 supporting a needle 20 therein for communicating the fluid which can be a medication or a nutrient, from the fluid carrying tube T which is shown in FIG. 7 through the closed end 18 to the cavity 15.

A second connector member 22 has a distal end 24 partially defining a flashback chamber, generally referred to as 26, and is adapted to pass through the open end 14 of the first connector member 12. Second connector member 22 includes external threads 28 thereon corresponding to the internal threads 16 of the first connector member. Threads 16 and 28 join both connector members 12, 22. Other fastening means such as a snap fastener or bayonet connection are equally suitable for joining connector members 12,22.

The second connector member 22 includes a rubber septum 30 on the distal end 24 partially defining the flashback chamber 26. Rubber septum 30 is yieldable and adapted to be penetrated by needle 20 when the first and second members 12, 22 are joined. Fluid communication is established through the needle 20 to the flashback chamber 26 when the first and second members 12, 22 are joined. This connection is accomplished without spillage and the rubber septum 30 spontaneously closes when the first and second connectors 12, 22 are separated and the needle 20 is withdrawn from the rubber septum.

The flashback chamber 26 also has a one way valve 32 that completes the definition of the flashback chamber and that is spaced from the needle 20 when the first and second connectors 12, 22 are joined. One way valve 32 is simple in construction and prevents the patient's blood from entering the flashback chamber 26 and thus prevents needle 20 from contacting the patient's blood while at the same time allowing for fluid communication through the needle.

With further reference to FIGS. 1 and 2 of the drawings, the second connector member 22 includes a cylindrical open end 34 on the second connector member opposite from the distal end 24. The one way valve 32 is a planar washer 36 spanning the open end 34 and is operable in one manner against the opened end (FIG. 3) to close the flashback chamber 26, for preventing blood from entering the chamber, and in another manner away from the opened end such as folded against annular shoulder 37, for passing fluid to the patient. The planar washer 36 is spaced axially from needle 20 for simplicity of construction and for allowing the medical connector 10 to be used for catheter placement as hereinafter described.

Figure 3:
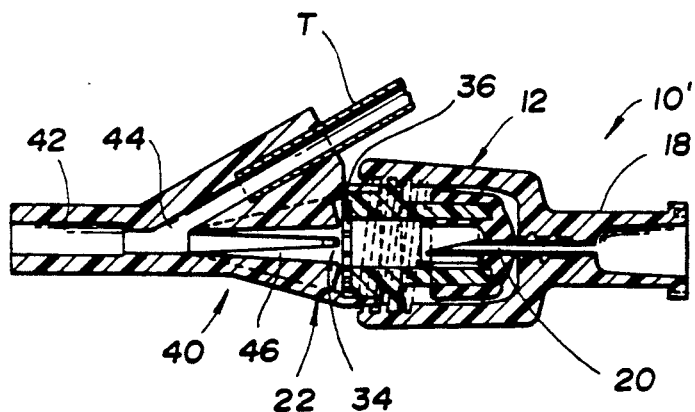
FIG. 3 is a sectional elevational view of the medical connector of FIG. 1 illustrated as a "Y"or piggyback connector in the second embodiment of the invention.

FIG. 3 of the drawings illustrates a second embodiment of the medical connector represented as 10'wherein the second connector member 22 includes a branch connection member 40 including first, second, and third tubular conduits numbered 42, 44, and 46, respectively. The first and second conduits 42, 44 merge into the third 46, and the third is in communication with the cylindrical open end 34 of the second connector member 22. A medical connector 10' so formed creates a conventional "Y" connector or piggyback connector which includes the flashback chamber 26 and one way valve 32 features of the present invention.

Figure 4:
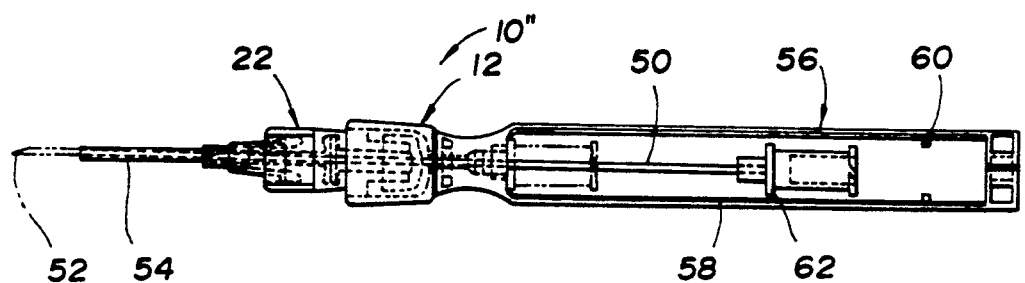
FIG. 4 is a plan view of the medical connector constructed in accordance with a third embodiment of the invention wherein the connector is used for venipuncture and insertion of a catheter.

In FIG. 4 of the drawings, the medical connector constructed in accordance with the third embodiment of the invention and referred to by 10" is illustrated. In this embodiment, the first connector member 12 includes an elongated introducer needle 50 having a tip 52 for venipuncture movably mounted with respect to the second closed end 18. The needle 50 is extendable beyond the first recessed open end 14 and cylindrical open end 34 of the second connector member 22 when the connector members 12, 22 are joined for introduction of the needle into the patient. As illustrated, the second connector member 22 includes a catheter tip 54 mounted on the cylindrical open end 34 through which the introducer needle 50 is movable. The catheter tip 54 is in communication with the flashback chamber 26.

The catheter tip 54 is insertable by the introducer needle 50 as the introducer needle is moved through the flashback chamber 26, the one way valve 32, the catheter tip 54 and through the tissues of the patient. The one way valve 32 comprises a resilient material which closes off a hole in the valve produced by the introducer needle 50 as the needle is moved into and out of the valve. The same rubber material used for the septum 30 is suitable for the one way valve 32.

With continued reference to FIG. 4 of the drawings, the medical connector 10" preferably includes a needle guard 56 extending from the second closed end 18 of the first connector member 12. The needle guard 56 includes an elongated guide 58 that houses the introducer needle 50. The needle guard 56 includes a stop 60 mounted in guide 58. The elongated introducer needle 50 includes a latch mechanism 62 on the end opposite from the tip 52 and cooperable with the stop 60 to hold the introducer needle in a retracted position where the tip of the introducer needle is recessed within the first recessed open end 14 of the first connector member 12.

Figure 5:
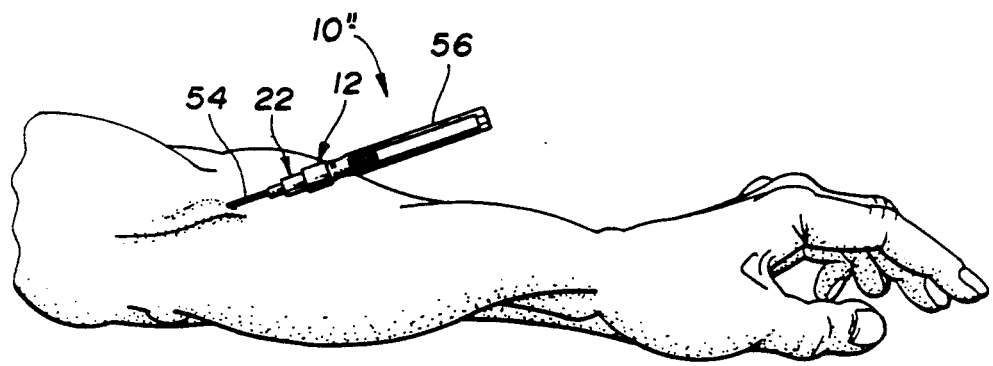
FIG. 5 is a schematic view illustrating the introduction of a catheter into a patient's arm using a connector constructed in accordance with the third embodiment.
Figure 6:
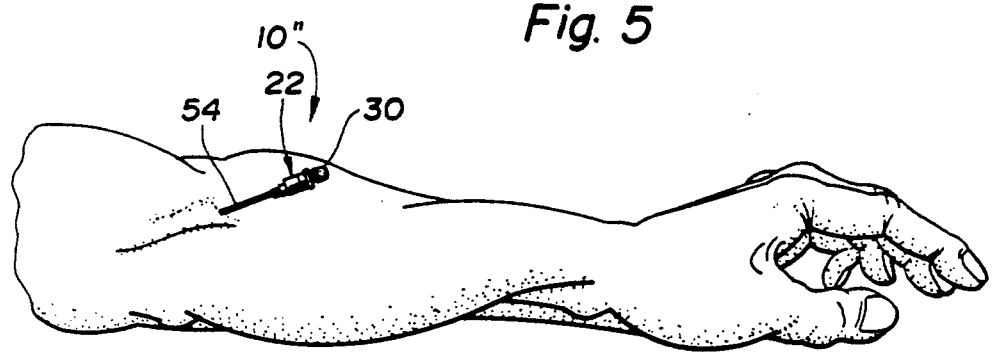
FIG. 6 is a schematic view similar to FIG. 5 illustrating one connector member and catheter extending from the patient's arm.

FIGS. 5 through 7 illustrate, through successive schematic illustrations, the use of the various embodiments of the connectors 10, 10', and 10"as a system for connecting fluid carrying tube T to a patient and for subsequent administration of a medication or nutrients to the patient.

In FIG. 6 of the drawings, medical connector 10" constructed in accordance with the third embodiment of the invention is used for the insertion of a catheter tip 54 in the patient. The second connector member 22 is subsequently disconnected from the first connector member 12 after the introducer needle 50 is retracted, as shown in FIG. 6, without the introduction of any amounts of blood into the flashback chamber 26.

In FIG. 7 of the drawings, a first connector member 12 constructed in accordance with the first embodiment of the invention is connected to the second connector member 22, constructed in accordance with the third embodiment of the invention to form a hybrid medical connector. This connection allows for the administration of medication or nutrients to the patient from tube T through the catheter tip 54. In addition, a medical connector 10', constructed in accordance with a second embodiment of the invention is shown whereby the branch connection member 40 allows two sources 64,64' of fluids to be communicated to the hybrid medical connector.

While the best mode for carrying out the invention has been described in detail, those familiar with the art to which this invention relates will recognize various alternative designs and embodiments for practicing the invention as defined by the following claims.

What is claimed is:

1. A medical connector for connecting a fluid carrying tube to a patient, the medical connector comprising:
   a first connector member having a first recessed open end defining a cavity including internal threads therein and a second closed end supporting a needle therein for communicating the fluid from the fluid carrying tube through said closed end to said cavity; and
   a second connector member having a distal end partially defining a flashback chamber and adapted to pass through the open end of said first connector member; said second connector member including external threads thereon corresponding to said internal threads of said first connector member for joining both connector members; said second connector member including a rubber septum on said distal end partially defining said flashback chamber and having a yieldable portion adapted to be penetrated by said needle when said first and second members are joined, whereby to establish fluid communication through said needle to said flashback chamber without spillage therefrom and for spontaneous closing when said first and second connectors are separated; said flashback chamber also having a one way valve completing the definition of said flashback chamber and spaced from said needle when said first and second connectors are joined, whereby to prevent the patient's blood from entering said chamber and establishing fluid communication through said needle.

2. A medical connector as in claim 1 wherein said second connector member includes a cylindrical open end on said second connector member opposite from the distal end thereof, said one way valve comprising a planar washer spanning said open end and operable in one manner against said open end to close said flashback chamber for preventing blood from entering said chamber and in another manner away from said open end for passing fluid to the patient.

3. A medical connector as in claim 2 wherein said planar washer is spaced axially from said needle.

4. A medical connector as in claim 1 wherein said flashback chamber is transparent allowing any blood entering said chamber to be viewed.

5. A medical connector as in claim 1 wherein said second connector member includes a branch connection member including first, second and third tubular conduits, said first and second conduits merging into said third and said third being in communication with said cylindrical open end of said second connector member.

6. A medical connector as in claim 1 wherein said first connector member includes an elongated introducer needle having a tip for venipuncture movably mounted with respect to said second closed end and extendable beyond said first recessed open end and said cylindrical open end of said second connector member when said connector members are joined for introduction of said needle into the patient; said second connector member also including a catheter tip mounted thereon said cylindrical open end through which said introducer needle is movable and being in communication with said flashback chamber; said catheter tip being inserted by said introducer needle into the patient; and said one way valve comprising a resilient material which closes off a hole in the valve produced by the introducer needle as said needle is moved into and out of said valve.

7. A medical connector as in claim 6 wherein said first connector member includes a needle guard extending from said second closed end, said needle guard including an elongated guide including a stop houses the introducer needle; said elongated introducer needle also including a latch mechanism on the end opposite from the tip and cooperable with said stop whereby to hold said introducer needle in a retracted position where the tip of the introducer needle is recessed within said first recessed open end.

* * * * *